United States Patent
Han et al.

(10) Patent No.: US 9,822,390 B2
(45) Date of Patent: Nov. 21, 2017

(54) HIGH-THROUGHPUT MUTAGENIZED CELL SCREENING SYSTEM FOR SELECTIVE SINGLE CELL EXTRACTION

(71) Applicant: THE TEXAS A&M UNIVERSITY SYSTEM, College Station, TX (US)

(72) Inventors: Arum Han, College Station, TX (US); Hyun Soo Kim, College Station, TX (US)

(73) Assignee: THE TEXAS A&M UNIVERSITY SYSTEM, College Station, TX (US)

(*) Notice: Subject to any disclaimer, the term of this patent is extended or adjusted under 35 U.S.C. 154(b) by 424 days.

(21) Appl. No.: 14/438,659

(22) PCT Filed: Oct. 28, 2013

(86) PCT No.: PCT/US2013/067062
§ 371 (c)(1),
(2) Date: Apr. 27, 2015

(87) PCT Pub. No.: WO2014/066888
PCT Pub. Date: May 1, 2014

(65) Prior Publication Data
US 2015/0291995 A1    Oct. 15, 2015

Related U.S. Application Data

(60) Provisional application No. 61/719,397, filed on Oct. 27, 2012.

(51) Int. Cl.
*C12Q 1/24* (2006.01)
*B01L 3/00* (2006.01)
(Continued)

(52) U.S. Cl.
CPC .......... *C12Q 1/24* (2013.01); *B01L 3/502753* (2013.01); *C12M 47/04* (2013.01);
(Continued)

(58) Field of Classification Search
CPC ....... B01L 2400/0481; B01L 2400/049; B01L 2400/06; B01L 2400/0633;
(Continued)

(56) References Cited

U.S. PATENT DOCUMENTS

2005/0194314 A1   9/2005  Lutz et al.
2006/0128006 A1   6/2006  Gerhardt et al.
(Continued)

FOREIGN PATENT DOCUMENTS

EP    2 078 958    7/2009

OTHER PUBLICATIONS

Kawai, Kentaro et al. "100 picoliter droplet handing using 256 microvalve array with 18 multiplexed control lines." Transducers (2009) p. 802-805.*

(Continued)

*Primary Examiner* — Christopher Adam Hixson
(74) *Attorney, Agent, or Firm* — Saliwanchik, Lloyd & Eisenschenk

(57) ABSTRACT

The subject invention pertains to a microfluidic apparatus and methods for screening and isolating a target cell from a population of cells. The apparatus comprises a first microfluidic layer comprising microfluidic channels; a second microfluidic layer comprising microfluidic channels; and a microfluidic cell analysis layer comprising a top hanging blocking structure located directly below each location where the first layer microfluidic channels overlap with the second layer microfluidic channels and a cell trap juxtaposed to each of the top hanging blocking structures. The top hanging blocking structures can close or open the juxtaposed cell trap when either or both the first or second layer microfluidic channels located directly above the top hanging blocking structure are sufficiently pressurized and/or sufficiently depressurized. The methods for screening and isolating a target cell from a population of cells comprise
(Continued)

screening the population of cells using the apparatus and isolating the target cell interest therefrom.

19 Claims, 7 Drawing Sheets

(51) Int. Cl.
    *G01N 33/50*     (2006.01)
    *C12M 1/00*     (2006.01)

(52) U.S. Cl.
    CPC .. *G01N 33/5005* (2013.01); *B01L 2200/0668* (2013.01); *B01L 2200/10* (2013.01); *B01L 2300/0636* (2013.01); *B01L 2300/0816* (2013.01); *B01L 2300/0887* (2013.01); *B01L 2300/123* (2013.01); *B01L 2400/0655* (2013.01); *B01L 2400/086* (2013.01)

(58) Field of Classification Search
    CPC ..... B01L 2400/0655; B01L 2400/0638; B01L 2400/065; B01L 2400/0661; B01L 3/502738

See application file for complete search history.

(56) References Cited

U.S. PATENT DOCUMENTS

2008/0194012 A1*   8/2008   Lee ................... B01L 3/502707
                                                  435/287.1
2010/0240041 A1     9/2010   Matsunaga et al.

OTHER PUBLICATIONS

Kim, H. S. et al. "High-Throughput Mutagenized Cell Screening System Capable of Selective Single Cell Extraction" *16th International Conference on Miniaturized Systems for Chemistry and Life Sciences*, Nov. 1, 2012, pp. 506-508.

Nilsson, J. et al. "Review of cell and particle trapping in microfluidic systems" *Analytica Chimica Acta*, 2009, pp. 141-157, vol. 649.

Written Opinion in International Application No. PCT/US2013/067062, dated Feb. 5, 2014, pp. 1-7.

Beer, L. L. et al. "Engeineering algae for biohydrogen and biofuel production" *Current Opinion in Biotechnology*, 2009, pp. 264-271, vol. 20.

Fabregas, J. et al. "Growth of the Marine Microalga *Tetraselmis suecica* in Batch Culture with Different Salinities and Nutrient Concentrations" *Aquaculture*, 1984, pp. 207-215, vol. 42.

Singh, U. et al. "Novel Live Alkaline Phosphatase Substrate for Identification of Pluripotent Stem Cells" *Stem Cell Rev and Rep*, 2012, pp. 1021-1029, vol. 8, No. 3.

Labrou, N. E. "Random Mutagenesis Methods for In Vitro Directed Enzyme Evolution" *Current Protein and Peptide Science*, 2010, pp. 91-100, vol. 11, No. 1.

* cited by examiner

HIGH-THROUGHPUT MUTAGENIZED CELL SCREENING SYSTEM FOR SELECTIVE SINGLE CELL EXTRACTION

CROSS-REFERENCE TO RELATED APPLICATIONS

This application is the U.S. national stage application of International Patent Application No. PCT/US2013/067062, filed Oct. 28, 2013, which claims the benefit of U.S. Provisional Application No. 61/719,397, filed Oct. 27, 2012, the contents of which are incorporated herein in their entirety.

BACKGROUND OF THE INVENTION

Many molecular and cell biology techniques involve identification and isolation of target cells from a population of cells. Some of these methods also require maintaining viability of the target cells after isolation. Thus, there is a need for screening apparatuses and methods that enable easy monitoring of target cells amongst the population of cells followed by selective extraction of the target cells for further analysis.

One such technique is mutagenesis in a population of cells. Mutagenesis is a powerful technique to produce target cells, for example, micro-organisms or cultured cells, capable of producing proteins, enzymes, or metabolites of interest. Coupled with screening or selection systems, mutagenesis has been successfully employed in various fields. Conventionally, screening and selection are conducted by culturing mutagenized populations, for example, mutagenized micro-organisms or cultured cells, at low dilution on culture plates and manually picking cells showing the desired trait. Although this process is useful and widely used, it is time-consuming and labor-intensive. Also, mutagenesis is costly and challenging because a large numbers of mutants (e.g. 1,000 to 1,000,000 mutants) may need to be screened to find one genetic variant showing the desired properties. Thus, there is also a need for a mutagenized cell screening platform that enables easy monitoring of mutagenized cells followed by selective extraction of a particular genetic variant of interest ("a hit") for further off-chip analysis and sampling.

BRIEF SUMMARY OF THE INVENTION

The current invention provides an apparatus for screening and selecting a target cell within a population of cells, the apparatus comprising:
  a) a first microfluidic control layer comprising one or more first layer microfluidic channels;
  b) a second microfluidic control layer comprising a one or more second layer microfluidic channels;
  wherein the one or more first layer microfluidic channels are not parallel to the one or more second layer microfluidic channels and each of the one or more first layer microfluidic channels overlaps with each of the one or more second layer microfluidic channels only once,
  and the one or more second layer microfluidic channels optionally contain top hanging ridge structures at every location where the one or more first layer microfluidic channels overlap with the one or more second layer microfluidic channels; and
  c) a microfluidic cell analysis layer comprising:
    A) a top hanging blocking structure located directly below each location where the first layer microfluidic channels overlap with the second layer microfluidic channels, and
    B) a cell trap juxtaposed to each of the top hanging blocking structures.

The apparatus of the current invention can be designed to operate in an "AND gate" mode or an "OR gate" mode. In these different modes, the top hanging blocking structures open or close the juxtaposed cell traps depending upon the pressure in the microfluidic channels directly above the top hanging blocking structures. These modes can be used to isolate a target cell or a subpopulation of target cells trapped in a particular cell trap of the microfluidic cell analysis layer.

The current invention also provides a method for screening and selecting a target cell within a population of cells, the method comprising:
  a) providing the population of cells,
  b) optionally, mutagenizing the population of cells,
  c) loading the population of cells into the apparatus of the current invention,
  d) conducting a bioassay to identify the target cell in the population of cells,
  e) isolating the target cell.

The apparatuses and the methods of the current invention can be used to isolate the target cell having a desirable characteristic, for example, presence of absence of a particular biomolecule, ability to produce a protein of interest, ability to produce a lipid of interest, ability to produce a metabolite of interest, or ability to grow in the presence or absence of an agent.

DETAILED DISCLOSURE OF THE INVENTION

Figure 1:
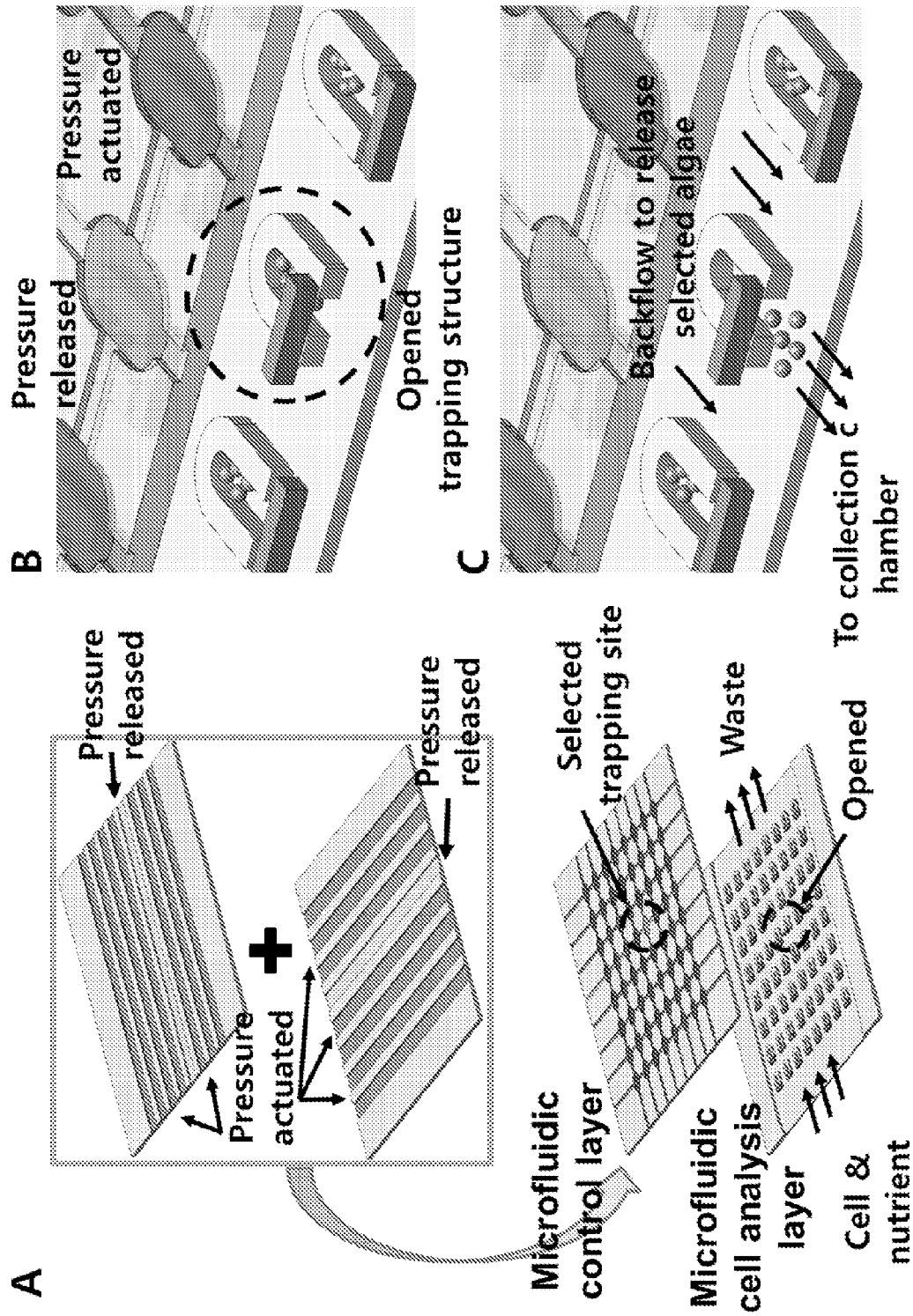
FIGS. 1A-1C. Illustration of a high-throughput cell screening apparatus in the AND gate mode. (A) Two PDMS functional layers—a microfluidic control layer and a microfluidic cell analysis layer. (B-C) Enlarged view of a selected cell trap where both the first and second layer microfluidic channel directly above the cell trap are sufficiently depressurized resulting in opened cell trap. Trapped cells can be extracted with backflow.

The terms "about", "approximately", "approximate" and "around" are used in this patent application to describe some quantitative aspects of the invention, for example, the height of certain embodiments. It should be understood that absolute accuracy is not required with respect to those aspects for the invention to operate. When these terms are used to describe a quantitative aspect of the invention the relevant aspect may be varied by up to ±10%. Thus, the terms "about", "approximately", "approximate" and "around" allow for variation of the various disclosed quantitative aspects of the invention by ±1%, ±2%, ±3%, ±4%, ±5%, ±6%, ±7%, ±8%, ±9% or up to ±10%.

The current invention provides an apparatus for screening and selecting a target cell within a population of cells. The apparatus of the current invention comprises:

a) a first microfluidic control layer comprising one or more first layer microfluidic channels;

b) a second microfluidic control layer comprising one or more second layer microfluidic channels, wherein the one or more first layer microfluidic channels are not parallel to the one or more second layer microfluidic channels and each of the one or more first layer microfluidic channels overlaps with each of the one or more second layer microfluidic channels only once, and one or more second layer microfluidic channels optionally contain top hanging ridge structures at every location where the one or more first layer microfluidic channels overlap with the one or more second layer microfluidic channels; and c) a microfluidic cell analysis layer comprising:
  A) a top hanging blocking structure located directly below each location where the first layer microfluidic channels overlap with the second layer microfluidic channels, and
  B) a cell trap juxtaposed to each of the top hanging blocking structures.

The apparatus of the current invention can be designed to operate in an "AND gate" mode or an "OR gate" mode. In these different modes, the top hanging blocking structures open or close the juxtaposed cell traps depending upon the pressure in the microfluidic channels directly above the top hanging blocking structures. These modes can be used to isolate a cell or subpopulation of cells trapped in a particular cell trap of the cell analysis layer.

In one embodiment of the invention, the first layer microfluidic channels are not parallel to the second layer microfluidic channels, i.e. the microfluidic channels of the first microfluidic control layer overlap with the microfluidic channels of the second microfluidic control layer. For the purposes of this invention, the phrase, "a microfluidic channel in the first layer overlaps with a microfluidic channel in the second layer" indicates that the microfluidic channel in the first layer crosses over and above the microfluidic channel in the second layer (i.e., without intersecting the microfluidic channel in the second layer). Further, each of the microfluidic channels of the first layer overlaps each of the microfluidic channels in the second layer only once, i.e. there is only one location where a given microfluidic channel of the first layer overlaps with a given microfluidic channel of the second layer and this overlap occurs at the site of a cell trap.

In certain embodiments of the invention, each of the one or more first layer microfluidic channels and/or the one or more second layer microfluidic channels are straight lines. In certain other embodiments, each of the one or more first layer microfluidic channels and/or the one or more second layer microfluidic channels are curved lines. In further embodiments, each of the one or more first layer microfluidic channels and/or the one or more second layer microfluidic channels are wave-form lines, for example, sinewave lines. In certain other embodiments, some of the one or more first layer microfluidic channels and/or some of the one or more second layer microfluidic channels are straight lines and some of the one or more first layer microfluidic channels and/or some of the one or more second layer microfluidic channels are curved lines or waveform lines.

Various grid patterns are formed due to various line forms, for example, straight lines, curved lines, or waveform lines, of the microfluidic channels of the first layer and the second layer. Examples of various grid patterns include, but are not limited to, straight microfluidic channels in the first layer overlapping with curved or waveform microfluidic channels in the second layer and vice versa, curved/waveform microfluidic channels in both the first and the second microfluidic layers, or straight line microfluidic channels in both the first and the second microfluidic layers.

In further embodiments of the invention, each of the one or more first layer microfluidic channels and the one or more second layer microfluidic channels are straight lines and the one or more first layer microfluidic channels overlap with the one or more second layer microfluidic channels to form a grid design comprising of a plurality of squares, rectangles, parallelograms, or *rhombi*.

In other embodiments, the number of one or more first layer microfluidic channels is equal to the number of one or more second layer microfluidic channels; whereas, in some embodiments the number of one or more first layer microfluidic channels is not equal to the number of one or more second layer microfluidic channels. In an embodiment of the invention, the number of one or more first layer microfluidic channels and the number of one or more second layer microfluidic channels is anywhere from 1 to 100. In another embodiment of the invention, the number of one or more first layer microfluidic channels and the number of one or more second layer microfluidic channels is 32.

In another embodiment of the invention the microfluidic channels of the apparatus of the current invention are pneumatically or hydraulically controlled channels.

The second layer microfluidic channels can contain top hanging ridge structures at every location where the one or more first layer microfluidic channels overlap with the one or more second layer microfluidic channels. The top hanging blocking structures located directly below each location where the first layer microfluidic channels overlap with the second layer microfluidic channels are juxtaposed to cell traps in such a way that the top hanging blocking structure can close the cell traps, i.e. does not allow the contents of the cell trap to escape when the top hanging blocking structure is sufficiently pushed downwards.

The distance between the cell trap and the top hanging blocking structure in a position where the cell trap is closed by the top hanging blocking structure can be adjusted depending upon the specific cell type being screened. For example, the distance between the cell trap and the top hanging blocking structure in a closed position is about 0.05 µM to about 0.5 µM if bacterial cells are screened. For eukaryotic cells (such as yeast or mammalian cells), the distance between the cell trap and the top hanging blocking structure in a closed position is about 0.5 µM to about 10 µM, about 2 µM to about 8 µM, or about 4 µM to about 6 µM.

The top hanging blocking structure can be sufficiently pushed downward to close the juxtaposed cell trap depending upon the AND gate mode or the OR gate mode of the apparatus and whether the first and/or second layer microfluidic channels are sufficiently pressurized or sufficiently depressurized. For the purposes of this invention, a microfluidic channel is sufficiently pressurized when the microfluidic channel has more than a minimum pressure which causes the top hanging blocking structures located directly below the microfluidic channel to close the juxtaposed cell trap; whereas, a microfluidic channel is sufficiently depressurized when the microfluidic channel has less than a maximum pressure which causes the top hanging blocking structure to open the juxtaposed cell trap.

In the AND gate mode, a top hanging blocking structure closes the juxtaposed cell trap when the second layer microfluidic channel located directly above the top hanging blocking structure is sufficiently pressurized and/or the first layer microfluidic channel overlapping the second layer microfluidic channel located directly above the top hanging blocking structure is sufficiently pressurized; whereas, the top hanging blocking structure opens the juxtaposed cell trap when the second layer microfluidic channel located directly above the top hanging blocking structure and the first layer microfluidic channel overlapping the second layer microfluidic channel located directly above the top hanging blocking structure are sufficiently depressurized.

The operation of a top hanging blocking structure in the AND gate mode can be summarized as shown in Table 1 below:

TABLE 1

| First layer microfluidic channel directly above the blocking structure | Second layer microfluidic channel directly above the blocking structure | Position of top hanging blocking structure relative to cell trap |
| --- | --- | --- |
| Pressurized | Pressurized | Closed |
| Pressurized | De-pressurized | Closed |
| De-pressurized | Pressurized | Closed |
| De-pressurized | De-pressurized | Open |

In the OR gate mode, a top hanging blocking structure closes the juxtaposed cell trap when the second layer microfluidic channel located directly above the top hanging blocking structure is sufficiently pressurized and the first layer microfluidic channel overlapping the second layer microfluidic channel located directly above the top hanging blocking structure is sufficiently pressurized; whereas, the top hanging blocking structure opens the cell trap when the second layer microfluidic channel located directly above the top hanging blocking structure and/or the first layer microfluidic channel overlapping the second layer microfluidic channel located directly above the top hanging blocking structure is sufficiently depressurized.

The operation of a top hanging blocking structure in the OR gate mode can be summarized as shown in Table 2 below:

TABLE 2

| First layer microfluidic channel directly above the blocking structure | Second layer microfluidic channel directly above the blocking structure | Position of top hanging blocking structure relative to cell trap |
| --- | --- | --- |
| Pressurized | Pressurized | Closed |
| Pressurized | De-pressurized | Open |
| De-pressurized | Pressurized | Open |
| De-pressurized | De-pressurized | Open |

In certain embodiments of the apparatus, for example, in the AND gate mode, the top hanging ridge structures in the second layer microfluidic channels facilitate the top hanging blocking structures of the analysis layer to close the juxtaposed cell traps when the first layer microfluidic channels are sufficiently pressurized but the second layer microfluidic channels are not sufficiently pressurized.

In the absence of the top hanging ridge structures in the second layer microfluidic channels, higher pressure is required in the first layer microfluidic channels to cause the top hanging blocking structure of the analysis layer to close the juxtaposed cell traps. For example, in the AND gate mode of the apparatus, to cause a top hanging blocking structure to close the juxtaposed cell trap in the absence of ridge structures and only with the first layer being sufficiently pressurized, a pressure of more than 50 psi is required since the first layer should be bent sufficiently to deform the second layer microfluidic channel, which then pushed down the top hanging blocking structure.

Therefore, the ridge structures in the second layer microfluidic channels are typically absent in the OR gate mode, i.e. when the pressurized first layer microfluidic channels do not cause the blocking structures to close the juxtaposed cell traps unless the second layer microfluidic channels are also sufficiently pressurized.

Figure 2:
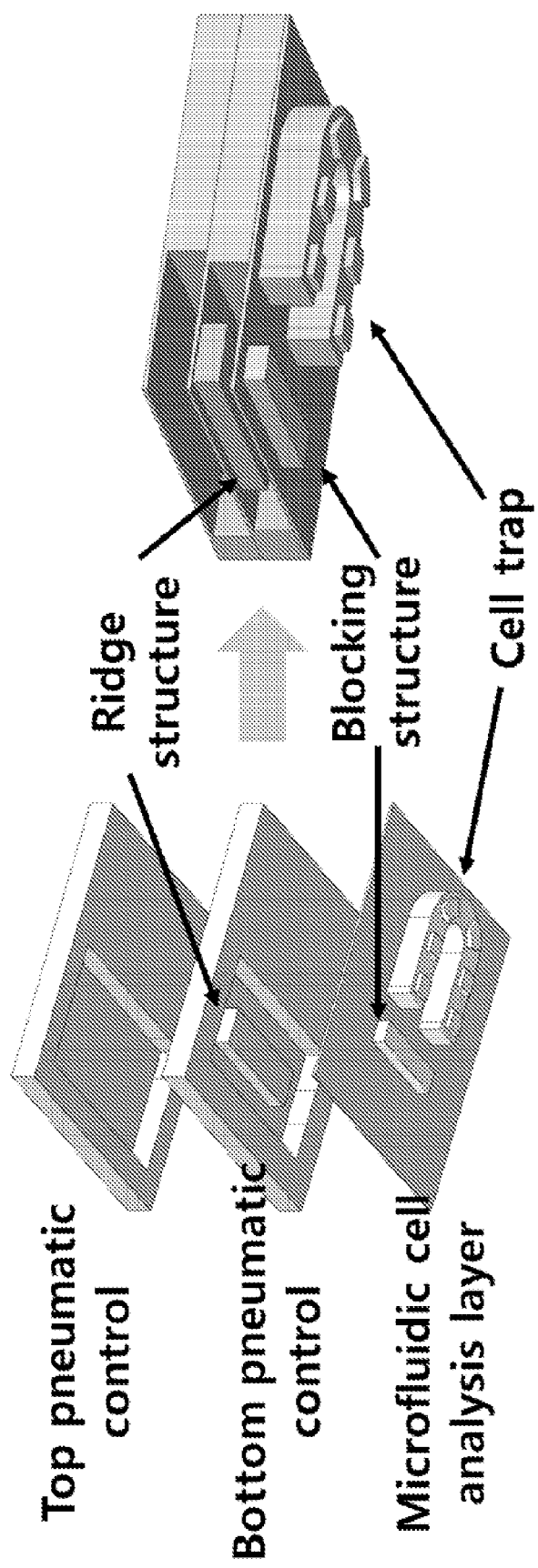
FIG. 2. A schematic view of a cell trap and pneumatic control microfluidic control layers. Each cell trapping site consists of a cell trap where one or more cells are captured and a top hanging blocking structure, which can be selectively opened and closed during the cell extraction process by changing the pressure in the microfluidic channels of the control layers. This design can be produced in an "inverted configuration" to produce an apparatus of the current invention which functions in the same way as the apparatus depicted in this figure but is physically inverted compared to the apparatus in this figure.
Figure 3:
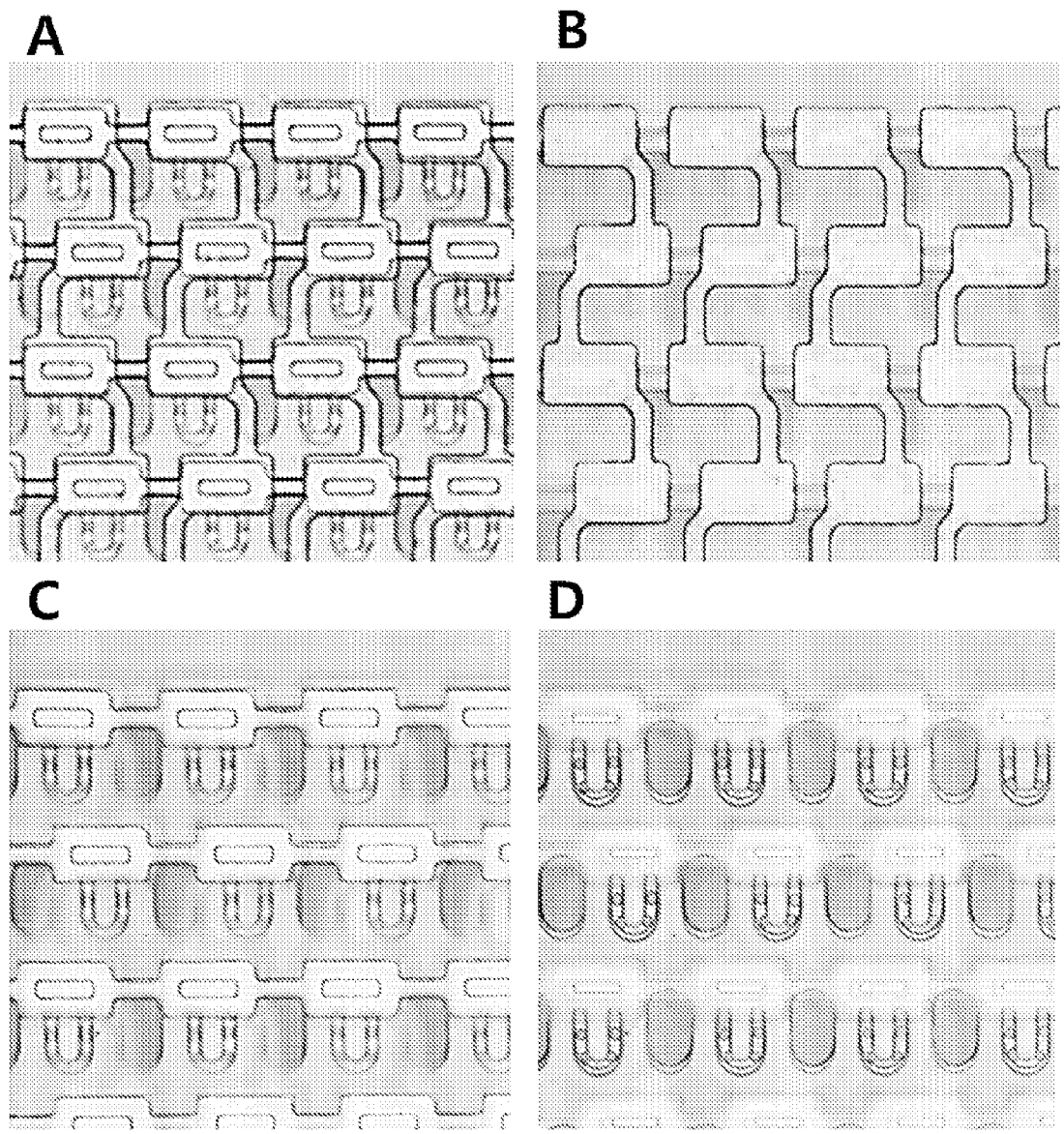
FIGS. 3A-3D. Microscopic images of the apparatus of the current invention. (A) An assembly showing all three layers—top and bottom pneumatic layers and a cell analysis layer. (B) Top pneumatic control layer. (C) Bottom pneumatic control layer. (D) Cell analysis layer.

To reduce the required pressure in the first layer microfluidic channels to cause a top hanging blocking structure to close the juxtaposed cell trap only with the first layer pressurization, e.g. in the AND gate mode apparatus, a top hanging ridge structure are typically present in the second layer microfluidic channel (FIG. 2). For example, in an embodiment of the invention, a top hanging ridge structures are positioned approximately 3 µM above the bottom surface in the middle of the second layer microfluidic channels. In such embodiments, when the first layer microfluidic channels are sufficiently pressurized it causes the second layer microfluidic channel to be deformed to a certain degree which causes the ridge structure to contact the top hanging blocking structure in the analysis layer and close the juxtaposed cell trap.

In certain embodiments of the apparatus of the current invention, the ridge structures which may be present in the second layer microfluidic channels are "top hanging", i.e. they are connected to the roof of the second layer microfluidic channels and hang therefrom. Similarly, in these embodiments the top hanging blocking structures in the cell analysis layers are "top hanging", i.e. they are connected to the roof of the cell analysis layer and hang therefrom.

For the purposes of the current invention, the height of an embodiment of the apparatus, for example, cell analysis layer, microfluidic control layer, cell trap, ridge structure, or blocking structure, indicates the dimension of the embodiment along the vertical axis as the apparatus is held in its working position.

In some embodiments of the apparatus of the current invention, the cell analysis layer is about 10-15 µM, about 16-20 µM, or about 21-25 µM high. In some other embodiments, the first microfluidic control layer is about 10-15 µM, about 16-20 µM, or about 21-25 µM high. In further embodiments, the second microfluidic control layer is also about 10-15 µM, about 16-20 µM, or about 21-25 µM high. In even further embodiments of the invention, apparatuses with various combinations of the heights of the cell analysis layer, the first microfluidic control layer, and the second microfluidic control layer as described above are provided.

In certain embodiments, the cell trap shaped in a manner that a cell or cells get trapped in the cell trap when fluids flow through the cell analysis layer in one direction; whereas, the cell or cells escape (if the blocking structure is in the open position) when the fluids flow through the cell analysis layer in the opposite direction. For example, the shape of the cell trap can be semicircular, substantially semicircular, horse shoe shaped, or C shaped. A person of ordinary skill in the art can design various shapes that can function to trap the cells. Such embodiments are within the purview of the current invention.

Also, the term "back flow" refers to the flow of the fluids through the analysis layer of the apparatus if the flow of the fluid facilitates the escape of the cell or cells trapped in the cell trap. Back flow can be used to collect the target cell or cells in the AND gate mode of the apparatus; whereas, back flow can be used to wash off the cells not of interest in the OR gate mode of the apparatus.

The cell trap is about 10-12 µM, about 13-16 µM, or about 17-20 µM high and based on the height of the cell trap and the mode of the apparatus (i.e. AND gate mode or OR gate mode), the top hanging blocking structure is about 5-10 µM, about 11-15 µM, or about 16-18 µM high.

In an embodiment of the invention, the apparatus is in the AND gate mode, and the cell analysis layer is about 15 µM high, the cell trap is about 12 µM high, and the top hanging blocking structure is about 8 µM high.

In another embodiment, the apparatus is in the OR gate mode, and the cell analysis layer is about 15 µM high, the cell trap is about 12 µM high, and the top hanging blocking structure is about 5 µM high.

Microfluidic channels in the apparatus of the current invention can have the diameter of about 0.1 µM to about 100 µM, about 1 µM to about 90 µM, about 5 µM to about 80 µM, about 10 µM to about 50 µM, about 20 µM to about 40 µM, or about 25 µM to about 30 µM. In an embodiment of the invention, the diameter of the microfluidic channels is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 µM.

In the AND gate mode, a top hanging blocking structure closes the juxtaposed cell trap when the second layer microfluidic channel located directly above the top hanging blocking structure is sufficiently pressurized and/or the first layer microfluidic channel overlapping the second layer microfluidic channel located directly above the top hanging blocking structure is sufficiently pressurized, i.e. a top hanging blocking structure closes the juxtaposed cell trap when at least one of the first or the second layer microfluidic channels located directly above the top hanging blocking structure is sufficiently pressurized. Also, in the AND gate mode, a top hanging blocking structure opens the juxtaposed cell trap when the second layer microfluidic channel located directly above the top hanging blocking structure is sufficiently depressurized and the first layer microfluidic channel overlapping the second layer microfluidic channel located directly above the top hanging blocking structure is sufficiently depressurized, i.e. a top hanging blocking structure opens the juxtaposed cell trap when both of the first and the second layer microfluidic channels located directly above the top hanging blocking structure are sufficiently depressurized.

In certain embodiments of the AND gate mode of the apparatus, a top hanging blocking structure closes the juxtaposed cell trap when the second layer microfluidic channel located directly above the top hanging blocking structure and/or the first layer microfluidic channel overlapping the second layer microfluidic channel located directly above the top hanging blocking structure is pressurized to at least about 15-20, about 21-25, about 26-30, about 31-35, about 36-40, about 41-45, about 46-50, or about 51-55 psi.

Also, in certain other embodiments of the AND gate mode of the apparatus, a top hanging blocking structure opens the juxtaposed cell trap when the second layer microfluidic channel located directly above the top hanging blocking structure and the first layer microfluidic channel overlapping the second layer microfluidic channel located directly above the top hanging blocking structure are pressurized to less than about 1-5, about 6-10, or about 11-15 psi.

In one such embodiment of the AND gate mode of the apparatus, the second layer microfluidic channels do not have any top hanging ridge structures, and a top hanging blocking structure closes the juxtaposed cell trap when the second layer microfluidic channel located directly above the top hanging blocking structure is pressurized to at least about 15-20, about 21-25, or about 26-30 psi and/or the first layer microfluidic channel overlapping the second layer microfluidic channel located directly above the top hanging blocking structure is pressurized to at least about 40-45, about 46-50, or about 51-55 psi. In a specific embodiment of the AND gate mode apparatus, the second layer microfluidic channels do not have any top hanging ridge structures, a top hanging blocking structure closes the juxtaposed cell trap when the second layer microfluidic channel located directly above the top hanging blocking structure is pressurized to at least about 18 psi and/or the first layer microfluidic channel overlapping the second layer microfluidic channel located directly above the top hanging blocking structure is pressurized to at least about 50 psi.

In one such embodiment of the AND gate mode of the apparatus, the second layer microfluidic channels do not have any top hanging ridge structures, and a top hanging blocking structure opens the juxtaposed cell trap when the second layer microfluidic channel located directly above the top hanging blocking structure and the first layer microfluidic channel overlapping the second layer microfluidic channel located directly above the top hanging blocking structure is pressurized to less than about 1-5, about 6-10, or about 11-15 psi. In another embodiment of the AND gate mode of the apparatus, the second layer microfluidic channels do not have any top hanging ridge structures, and a top hanging blocking structure opens the juxtaposed cell trap when the second layer microfluidic channel located directly above the top hanging blocking structure and the first layer microfluidic channel overlapping the second layer microfluidic channel located directly above the top hanging blocking structure is pressurized to less than about 11-15 psi.

In a further embodiment of the AND gate mode of the apparatus, the second layer microfluidic channels have the top hanging ridge structures at every location where the first layer microfluidic channels overlap with the second layer microfluidic channels, and a top hanging blocking structure closes the juxtaposed cell trap when the second layer microfluidic channel located directly above the top hanging blocking structure is pressurized to at least about 15-20, about 21-25, or about 26-30 psi and/or the first layer microfluidic channel overlapping the second layer microfluidic channel located directly above the top hanging blocking structure is pressurized to at least about 25-30 or about 31-35 psi. In an embodiment of the AND gate mode apparatus, the second layer microfluidic channels have the top hanging ridge structures at every location where the first layer microfluidic channels overlap with the second layer microfluidic channels, a top hanging blocking structure closes the juxtaposed cell trap when the second layer microfluidic channel located directly above the top hanging blocking structure is pressurized to at least about 18 psi and/or the first layer microfluidic channel overlapping the second layer microfluidic channel located directly above the top hanging blocking structure is pressurized to at least about 30 psi.

In one such embodiment of the AND gate mode of the apparatus, the second layer microfluidic channels have the top hanging ridge structures at every location where the first layer microfluidic channels overlap with the second layer microfluidic channels, a top hanging blocking structure opens the juxtaposed cell trap when the second layer microfluidic channel located directly above the top hanging blocking structure and the first layer microfluidic channel overlapping the second layer microfluidic channel located directly above the top hanging blocking structure is pressurized to less than about 1-5, about 6-10, or about 11-15 psi. In another embodiment of the AND gate mode of the apparatus, the second layer microfluidic channels have the top hanging ridge structures at every location where the first layer microfluidic channels overlap with the second layer microfluidic channels, a top hanging blocking structure opens the juxtaposed cell trap when the second layer microfluidic channel located directly above the top hanging blocking structure and the first layer microfluidic channel overlapping the second layer microfluidic channel located directly above the top hanging blocking structure is pressurized to less than about 1-5 psi.

In the AND gate mode of the apparatus, various combinations of minimum or maximum pressures in the first and/or the second layer microfluidic channels to allow opening or closing of the cell traps by the juxtaposed top hanging blocking structures depend on, among other things, the following aspects of the apparatus:

a) the elasticity of the material used to produce the apparatus;
b) the presence or absence of ridge structures in the second layer microfluidic channels;
c) if present, the height of the ridge structures;
d) the height of the top hanging blocking structures; and
e) the height of the cell trap.

A person of ordinary skill in the art can decipher various combinations of minimum or maximum pressures in the first and/or the second layer microfluidic channels to allow opening or closing of the cell traps by the juxtaposed top hanging blocking structures by varying the above mentioned aspects of the apparatus and such embodiments are within the purview of the current invention.

In the OR gate mode, a top hanging blocking structure closes the juxtaposed cell trap when the second layer microfluidic channel located directly above the top hanging blocking structure is sufficiently pressurized and the first layer microfluidic channel overlapping the second layer microfluidic channel located directly above the top hanging blocking structure is sufficiently pressurized, i.e. a top hanging blocking structure closes the juxtaposed cell trap when both of the first and the second layer microfluidic channels located directly above the top hanging blocking structure are sufficiently pressurized. Also, in the OR gate mode, a top hanging blocking structure opens the juxtaposed cell trap when the second layer microfluidic channel located directly above the top hanging blocking structure is sufficiently depressurized and/or the first layer microfluidic channel overlapping the second layer microfluidic channel directly above the top hanging blocking structure is sufficiently depressurized, i.e. a top hanging blocking structure opens the juxtaposed cell trap when at least one of the first and the second layer microfluidic channels located directly above the top hanging blocking structure is sufficiently depressurized.

In an embodiment of the OR gate mode of the apparatus, a top hanging blocking structure closes the juxtaposed cell trap when both the second layer microfluidic channel located directly above the top hanging blocking structure and the first layer microfluidic channel overlapping the second layer microfluidic channel located directly above the top hanging blocking structure are pressurized to at least about 15-20, about 21-25, about 26-30, about 31-35, about 36-40, about 41-45, about 46-50, or about 51-55 psi.

Also, in another embodiment of the OR gate mode of the apparatus, a top hanging blocking structure opens the juxtaposed cell trap when the second layer microfluidic channel located directly above the top hanging blocking structure and/or the first layer microfluidic channel overlapping the second layer microfluidic channel located directly above the top hanging blocking structure is pressurized to less than about 1-5, about 6-10, or about 11-15 psi.

In one such embodiment of the OR gate mode of the apparatus, the second layer microfluidic channels do not have any top hanging ridge structures, a top hanging blocking structure closes the juxtaposed cell trap when the second layer microfluidic channel located directly above the top hanging blocking structure is pressurized to at least about 15-20, about 21-25, or about 26-30 psi and the first layer microfluidic channel overlapping the second layer microfluidic channel located directly above the top hanging blocking structure is pressurized to at least about 40-45, about 46-50, or about 51-55 psi. In a specific embodiment of the OR gate mode apparatus where the second layer microfluidic channels do not have any top hanging ridge structures, a top hanging blocking structure closes the juxtaposed cell trap when the second layer microfluidic channel located directly above the top hanging blocking structure is pressurized to at least about 18 psi and the first layer microfluidic channel overlapping the second layer microfluidic channel located directly above the top hanging blocking structure is pressurized to at least about 50 psi.

In other embodiments of the OR gate mode of the apparatus, the second layer microfluidic channels do not have the top hanging ridge structures, a top hanging blocking structure opens the juxtaposed cell trap when the second layer microfluidic channel located directly above the top hanging blocking structure and/or the first layer microfluidic channel overlapping the second layer microfluidic channel located directly above the top hanging blocking structure is pressurized to less than about 1-5, about 6-10, or about 11-15 psi. In another embodiment of the OR gate mode of the apparatus, the second layer microfluidic channels do not have the top hanging ridge structures, a top hanging blocking structure opens the juxtaposed cell trap when the second layer microfluidic channel located directly above the top hanging blocking structure and/or the first layer microfluidic channel overlapping the second layer microfluidic channel located directly above the top hanging blocking structure is pressurized to less than about 11-15 psi.

In a further embodiment of the OR gate mode of the apparatus, the second layer microfluidic channels have the top hanging ridge structures at every location where the first layer microfluidic channels overlap with the second layer microfluidic channels, a top hanging blocking structure closes the juxtaposed cell trap when the second layer microfluidic channel located directly above the top hanging blocking structure is pressurized to at least about 15-20, about 21-25, or about 26-30 psi and the first layer microfluidic channel overlapping the second layer microfluidic channel located directly above the top hanging blocking structure is pressurized to at least about 25-30 or about 31-35 psi. In an embodiment of the OR gate mode apparatus, the second layer microfluidic channels have the top hanging ridge structures at every location where the first layer microfluidic channels overlap with the second layer microfluidic channels, and a top hanging blocking structure closes the juxtaposed cell trap when the second layer microfluidic channel located directly above the top hanging blocking structure is pressurized to at least about 18 psi and the first layer microfluidic channel overlapping the second layer microfluidic channel located directly above the top hanging blocking structure is pressurized to at least about 30 psi.

In one such embodiment of the OR gate mode of the apparatus, the second layer microfluidic channels have the top hanging ridge structures at every location where the first layer microfluidic channels overlap with the second layer microfluidic channels, a top hanging blocking structure opens the juxtaposed cell trap when the second layer microfluidic channel located directly above the top hanging blocking structure and/or the first layer microfluidic channel overlapping the second layer microfluidic channel located directly above the top hanging blocking structure is pressurized to less than about 1-5, about 6-10, or about 11-15 psi. In another embodiment of the OR gate mode of the apparatus, the second layer microfluidic channels have the top hanging ridge structures at every location where the first layer microfluidic channels overlap with the second layer microfluidic channels, a top hanging blocking structure opens the juxtaposed cell trap when the second layer microfluidic channel located directly above the top hanging blocking structure and/or the first layer microfluidic channel overlapping the second layer microfluidic channel located directly above the top hanging blocking structure is pressurized to less than about 1-5 psi.

In the OR gate mode of the apparatus, various combinations of minimum or maximum pressures in the first and/or the second layer microfluidic channels to allow opening or closing of the cell traps by the juxtaposed top hanging blocking structures depend on, among other things, the following aspects of the apparatus:

a) the elasticity of the material used to produce the apparatus;
b) the presence or absence of ridge structures in the second layer microfluidic channels;
c) if present, the height of the ridge structures;
d) the height of the top hanging blocking structures; and
e) the height of the cell trap.

A person of ordinary skill in the art can decipher various combinations of minimum or maximum pressures in the first and/or the second layer microfluidic channels to allow opening or closing of the cell traps by the juxtaposed top hanging blocking structures by varying the above mentioned aspects of the apparatus and such embodiments are within the purview of the current invention.

The AND gate and the OR gate modes of the apparatus of the current invention facilitate the collection of a target cell or cells located in a particular cell trap. The details of the methods used to collect cell or cells located in a particular cell trap from the AND gate mode or the OR gate mode apparatus are discussed below in connection with the methods of the current invention.

The apparatus of current invention can be wholly or partly made from an elastic material, i.e. solid materials that return to their original shape after being deformed, for example under force or pressure. In certain embodiments, the apparatus of the current invention is wholly made from an elastic material, for example, an elastomer. In other embodiments, the apparatus of the current invention is partly made from an elastic material, for example, an elastomer, and partly made from a non-elastic or a rigid material.

The elastic material can be an elastomer. An elastomer is a polymer with elasticity, generally having low Young's modulus, and high failure strain compared with other materials. In certain embodiments of the invention, the elastomer used to produce the apparatus of the current invention is transparent or substantially transparent to light, for example, visible light, infrared, or ultraviolet light.

Non-limiting examples of elastomers that can be used to produce the apparatus of the current invention include thermoplastic elastomers, styrenic materials, olefenic materials, polyolefin, polyurethane thermoplastic elastomers, polyamides, synthetic rubbers, silicon-based organic polymers, polybutadiene, polyisobutylene, poly(styrene-butadiene-styrene), polyurethanes, polychloroprene and silicones. In an embodiment, the apparatus of the current invention is made of polydimethylsiloxane (PDMS).

The rigid material can be a rigid plastic material. Non-limiting examples of rigid plastic materials include polystyrene, polycarbonate, polyethylene, polyvinyl chloride, and polypropylene. Additional examples of rigid plastic materials are well known to a person of ordinary skill in the art and such embodiments are within the purview of the current invention.

In an apparatus of the current invention, all the three layers of the apparatus can also be made from an elastic material. In certain embodiments, the three layers of the apparatus are made from the same type of elastic material or different types of elastic materials.

In other embodiments of the current invention, the cell analysis layer is made from a rigid material; whereas, the first and the second microfluidic control layers are made from one or more elastic materials. In certain other embodiments, the cell analysis layer is partly made from an elastic material and partly made from a rigid material.

In further embodiments of the invention, the first and/or the second microfluidic control layers are partly made from one or more elastic materials and partly made from one or more rigid materials. When the first and/or the second microfluidic control layers are partly made from one or more elastic materials and partly made from one or more rigid materials, the portions surrounding the microfluidic channels along the longitudinal axes of the channels, the ridge structures (if present), and the blocking structures are made from one or more elastic materials; whereas the rest of the first and the second microfluidic layers can be made from one or more rigid materials. Such designs allow for normal operation of the apparatus, for example, desired mobility in the microfluidic channels, ridge structures (if present), and blocking structures, while providing structural strength to the apparatus. A person of ordinary skill in the art can determine various combinations of whole or part of the fabrication materials of the cell analysis layer and the first and the second microfluidic control layers and such combinations are within the purview of the current invention. In a further embodiment of the invention, a protective layer of rigid material is present on top of the first microfluidic control layer and/or at the bottom of the cell analysis layer.

The current invention also provides a method for screening and isolating a target cell within a population of cells using the apparatus of the current invention. The method of the current invention comprises:
  a) providing the population of cells,
  b) optionally, mutagenizing the population of cells,
  c) loading the population of cells into the apparatus of the current invention,
  d) conducting a bioassay to identify the target cell in the population of cells,
  e) isolating the target cell from the apparatus.

The target cell can be isolated from the AND gate mode apparatus by:
  a) sufficiently pressurizing all of the first layer microfluidic channels and all of the second layer microfluidic channels thereby closing all cell traps,
  b) opening only the cell trap containing the target cell by:
    A) sufficiently depressurizing only that second layer microfluidic channel which is directly above the cell trap containing the target cell, and
    B) sufficiently depressurizing only that first layer microfluidic channel which is overlapping the microfluidic channel directly above the cell trap containing the target cell,
  c) extracting the target cell from the cell trap and collecting the target cell.

Figure 4:
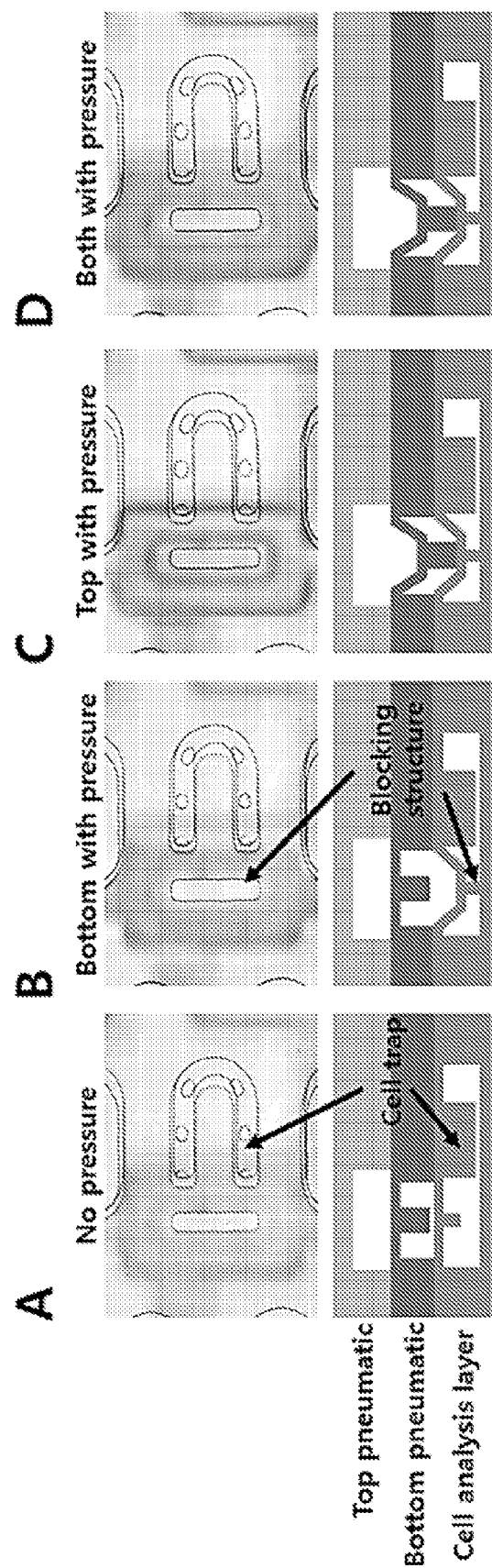
FIGS. 4A-4D. Micrographs and schematics of the single cell trap, which show the operation of the top hanging blocking structure in the AND gate mode. (A) During cell loading, culturing, and analysis, no pressure is applied and all top hanging blocking structures as well as all cell traps are open. (B-D) During the extraction process, pressure is applied to one of the two pneumatic layers or to both, resulting in closure of the cell traps. Only the particular cell trap stays open during this process because both microfluidic channels directly above the cell trap of interest are simultaneously depressurized, as shown in (A).
Figure 5:
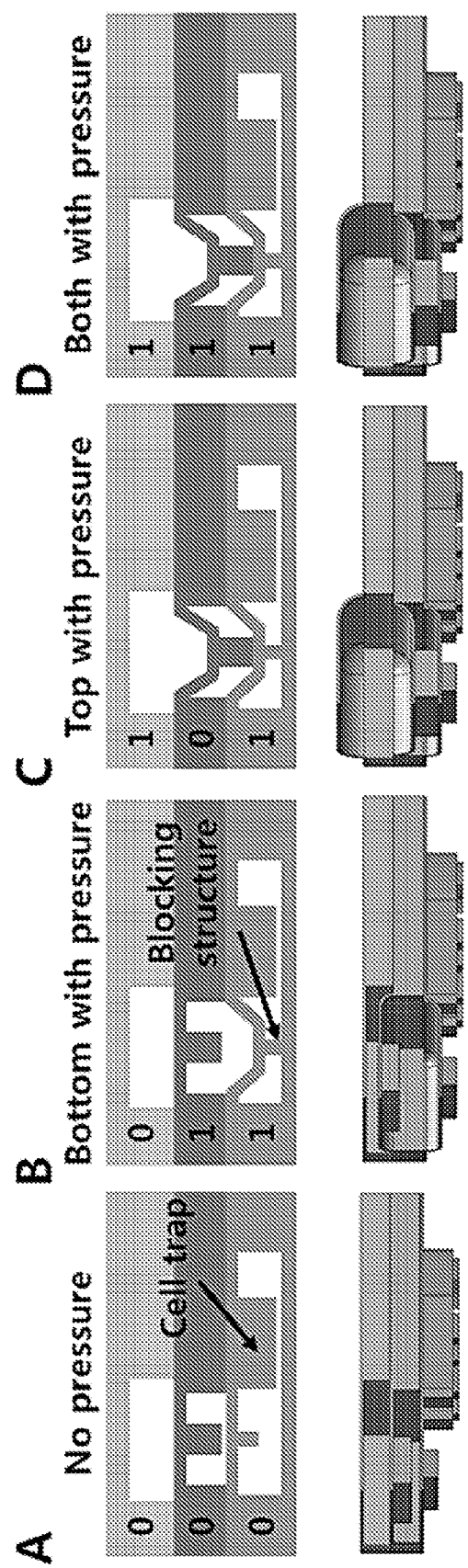
FIGS. 5A-5D. Schematics of the single cell trap which illustrates the operation of the top hanging blocking structure for the opening and closing of the juxtaposed cell trap according to the AND gate mode of the apparatus. 5A: No pressure; 5B: Bottom with pressure; 5C: Top with pressure; and 5D: Both with pressure. "0" indicates opening of the selected cell trap and "1" indicates the closing of the selected cell trap.

An example of a procedure to collect a target cell or cells from the AND gate mode apparatus is depicted in FIG. 4.

The target cell or cells can be isolated from the OR gate mode apparatus by:
  a) sufficiently pressurizing all of the first layer microfluidic channels and all of the second layer microfluidic channels thereby closing all cell traps,
  b) opening of all the cell traps except the cell trap containing the target cell or cells by:
    A) sufficiently depressurizing all the second layer microfluidic channels except the second layer microfluidic channel which is directly above the cell trap containing the target cell, and
    B) sufficiently depressurizing all the first layer microfluidic channels except the first layer microfluidic channel which is overlapping the second layer microfluidic channel directly above the cell trap containing the target cell,
  c) washing off all the cell traps to remove the cells except the target cell or cells trapped in the target cell trap,
  d) collecting the target cell or cells by:
    A) sufficiently depressurizing the second layer microfluidic channel directly above the cell trap containing the target cell or cells, and/or
    B) sufficiently depressurizing the first layer microfluidic channel which is overlapping the second layer microfluidic channel directly above the cell trap containing the target cell.

The cell or cells inside this particular cell trap can be then extracted and collected to off-chip reservoirs for further analysis.

Using these schemes, the number of controlled microfluidic channel can be minimized. For example, to control 1024 cell traps (32 by 32) individually, a conventional method would require 1024 individually controllable microfluidic channels. However in this scheme, all 1024 cell traps can be controlled by 32+32 control microfluidic channels. The number of control channels can be further reduced by utilizing a microfluidic multiplexer, as known in the prior art.

Sometimes more than one type of cell or cells can be present in a cell trap. For example, a cell trap of interest can have one or more target cells of interest and one or more cells that are not of interest. In such situations, the cells in the cell trap of interest can be collected as described above by the AND gate mode or the OR gate mode apparatus. These cells can be re-introduced in the apparatus of the current invention to isolate the cell or cells of interest via another cycle of distribution of the cells in to the various cell traps of the apparatus and collection of the cell or cells of interest by procedures described above.

In certain embodiments of the current invention, the population of cell comprises prokaryotic cells or eukaryotic cells. The prokaryotic cells comprise bacterial cells or cyanobacterial cells; whereas, eukaryotic cells can be yeast cells, fungal cells, protozoan cells, eukaryotic algal cells, or mammalian cells. The mammalian cells can be cultured cells or cells isolated from a mammal, for example, blood cells or any other type of cells.

The population of cells can be mutagenized to produce a genetic variant of interest. A number of ways to mutagenize a population of cells are well known to a person of ordinary skill in the art. Mutagenesis in the population of cells can be done by exposing the cells to mutagenic agents such as x-rays or mutagenic chemicals. Various ways of mutagenizing a population of cells and a number of mutagens are well known to person of ordinary skill in the art such methods of mutagenesis and use of the mutagens is within the purview of the current invention.

A person of ordinary skill in the art can also recognize that the apparatuses and methods of the current invention can be used to isolate a cell or cells of interest in a population of cells, i.e. the cell may be a cell of a particular type in a population of cells of different types.

The bioassay conducted to identify the target cell is designed in a manner that allows the cells being examined to remain alive after the bioassay is conducted.

In certain embodiments, the bioassay conducted to identify the target cell comprises light microscopy or fluorescent microscopy. In certain other embodiments, the bioassay comprises microscopic observation of the cells trapped in various cell traps to identify the target cell that exhibits a morphologic phenotype identifiable by microscopic observation. Non-limiting examples of morphological phenotypes include larger or smaller cell size, or cells having a specific shape, cells in the stage of cell division.

If the target cell involves some other criteria, for example, accumulation of lipid, expression of a protein of interest, or synthesis of a metabolite, the bioassay used to identify the cell of interest can be designed accordingly.

For example, to identify a target cell accumulating higher or lower amount of intracellular lipid the cells can be stained with a live lipid stain which stains the lipids inside the cell without killing the cell. The cells trapped in various cell traps can be observed under the microscope to identify the target cell having higher or lower amounts of accumulated lipid.

To identify a cell expressing or not expressing a target protein, antibodies tagged with fluorescent dyes capable binding to the target protein can be used. Non-limiting examples of a protein of interest can be an enzyme, an antibody or a fragment thereof, a pharmaceutically active protein, and a protein carrying a specific mutation.

The target protein can be a cell surface protein or a cytosolic protein. If the target protein is a cytosolic protein, cell can be permeabilized to allow the antibody to enter the cell and bind to the target protein. Cell permeabilization can be done by treatment with mild detergents, for example, digitonin or saponin. Additional protocols allowing binding of an antibody to an intracellular target protein without damaging or killing the cell are well known to a person of ordinary skill in the art and such embodiments are within the purview of the current invention.

To isolate a cell expressing or not expressing a target protein, an antibody tagged with a fluorescent dye and having binding specificity for the protein of interest can be administered to cell analysis layer of the apparatus. Upon sufficient incubation time to allow the binding between the antibody and the corresponding protein, the target cell expressing or not expressing the target protein can be identified under a fluorescent microscope. The target cell can then be isolated from the cell trap.

If the target protein of interest is an enzyme, the bioassay used to identify the presence or absence of the enzyme in the cells can comprise of chromogenic enzymatic assay that does not damage or kill the cell having the enzyme, such assay can be used to identify the target cell. For example, a cell containing alkaline phosphatase can be identified by a chromogenic assay that does not damage or kill the cell. An example of such assay is described by Singh et al.[4]

The bioassay used to identify a target cell can be designed to identify the target cell capable of growing or not growing in the presence or absence of an agent. Non-limiting examples of the agent can be an antibiotic, a growth inhibitor, a metabolite.

Additional examples of bioassays that can identify a target cell within a cell population without damaging or killing the target cell are known to a person of ordinary skill in the art and such embodiments are within the purview of the current invention.

The description of the embodiments of the apparatus of the current invention as detailed above envisions that the first microfluidic control layer is on top of the second microfluidic control layer, which in turn is on top of the cell analysis layer. In these embodiments, as described throughout the application, the ridge structures which may be present in the second layer microfluidic channels are "top hanging", i.e. they are connected to the roof of the second layer microfluidic channels and hang therefrom. Similarly, in these embodiments the top hanging blocking structures in the cell analysis layers are "top hanging", i.e. they are connected to the roof of the cell analysis layer and hang therefrom.

The current invention also provides the "inverted versions" of apparatus described above. In the "inverted versions", the first microfluidic control layer is below the second microfluidic control layer, which in turn below the cell analysis layer. In these embodiments, the ridge structures which may be present in the second layer microfluidic channels are "lying on the bottom", i.e. they are connected to the bottom of the second layer microfluidic channels and stand upon it. Similarly, in these embodiments the blocking structures in the cell analysis layers are "lying on the bottom", i.e. they are connected to the bottom of the cell analysis layer and stand above it. Based on the disclosure of the current invention, a person of ordinary skill in the art can produce such inverted versions of the apparatus of the current invention and such inverted embodiments are within the purview of the current invention.

Certain embodiments of the current invention are described below:

Embodiment 1

An apparatus for screening and selecting a target cell within a population of cells, the apparatus comprising:

a first layer comprising a first top-hanging structure that is stationary and functions as a cell trap to trap a single cell or sub-population of cells, and a second top-hanging structure having a different height relative to the first top-hanging structure, wherein the second top-hanging structure is mobile and functions as a gate to open or close the cell trap;

a second layer comprising a plurality of microfluidic channels in rows; and a third layer comprising the same number of microfluidic channels in rows as the second layer, wherein the microfluidic channel rows in the third layer are located in a perpendicular direction to the microfluidic channel rows in the second layer;

wherein the second and third layers combine to function as a microfluidic logic AND gate where the microfluidic channels in the second layer and the third layer function as two inputs to the AND gate and the up and down movement of the second top-hanging gate structure is the output of the AND gate.

Embodiment 2

An apparatus for screening and selecting a target cell within a population of cells, the apparatus comprising:

a) a first microfluidic control layer comprising one or more first layer microfluidic channels;

b) a second microfluidic control layer comprising a one or more second layer microfluidic channels, wherein the one or more first layer microfluidic channels are not parallel to the one or more second layer microfluidic channels and each of the one or more first layer microfluidic channels overlaps with each of the one or more second layer microfluidic channels only once, and and the one or more second layer microfluidic channels optionally contain top hanging ridge structures at every location where the one or more first layer microfluidic channels overlap with the one or more second layer microfluidic channels; and c) a microfluidic cell analysis layer comprising:

A) a top hanging blocking structure located directly below every location where the first layer microfluidic channels overlap with the second layer microfluidic channels, and B) a cell trap juxtaposed to each of the top hanging blocking structures.

Embodiment 3

The apparatus of embodiment 2, wherein the top hanging blocking structure closes the juxtaposed cell trap when the second layer microfluidic channel located directly above the top hanging blocking structure is sufficiently pressurized and/or the first layer microfluidic channel overlapping the second layer microfluidic channel located directly above the top hanging blocking structure is sufficiently pressurized, and wherein the top hanging blocking structure opens the cell trap when the second layer microfluidic channel located directly above the top hanging blocking structure and the first layer microfluidic channel overlapping the second layer microfluidic channel located directly above the top hanging blocking structure are sufficiently depressurized.

Embodiment 4

The apparatus of embodiment 2, wherein the top hanging blocking structure closes the juxtaposed cell trap when the second layer microfluidic channel located directly above the top hanging blocking structure is sufficiently pressurized and the first layer microfluidic channel overlapping the second layer microfluidic channel located directly above the top hanging blocking structure is sufficiently pressurized, and wherein the top hanging blocking structure opens the juxtaposed cell trap when the second layer microfluidic channel located directly above the top hanging blocking structure and/or the first layer microfluidic channel overlapping the second layer microfluidic channel located directly above the top hanging blocking structure is sufficiently depressurized.

Embodiment 5

The apparatus of any of embodiments 1-4 made wholly from an elastic material.

Embodiment 6

The apparatus of any of embodiments 1-4 made partly from an elastic material and party from a rigid material.

Embodiment 7

The apparatus of any of embodiments 5-6, wherein the elastic material is an elastomer.

Embodiment 8

The apparatus of embodiment 7, wherein the elastomer is selected from thermoplastic elastomers, styrenic materials, olefenic materials, polyolefin, polyurethane thermoplastic elastomers, polyamides, synthetic rubbers, silicon-based organic polymers, polybutadiene, polyisobutylene, poly(styrene-butadiene-styrene), polyurethanes, polychloroprene and silicones.

Embodiment 9

The apparatus of embodiment 8, wherein the silicon-based organic polymer is polydimethylsiloxane (PDMS).

Embodiment 10

The apparatus of embodiment 6, wherein the rigid material is a plastic material.

Embodiment 11

The apparatus of embodiment 10, wherein the plastic material is polystyrene, polycarbonate, polyethylene, polyvinyl Chloride, or polypropylene.

Embodiment 12

The apparatus of embodiment 6, wherein the cell analysis layer is made from the rigid material and the first and the second microfluidic control layers are made from the elastic material.

Embodiment 13

The apparatus of embodiment 6, wherein the cell analysis layer is partly made from the elastic material and partly made from the rigid material.

Embodiment 14

The apparatus of embodiment 6, wherein the first and/or the second microfluidic control layer is partly made from the elastic material and partly made from the rigid material, and wherein the portions surrounding the microfluidic channels along the longitudinal axes of the channels, the ridge structures (if present), and the blocking structures are made from the elastic material and the rest of the portions of the first and the second microfluidic control layers are made from the rigid material.

Embodiment 15

The apparatus of any of embodiments 1-14, further comprising a protective layer of the rigid material on top of the first microfluidic control layer and/or at the bottom of the cell analysis layer.

Embodiment 16

The apparatus of any of embodiments 1-15, wherein each of the one or more first layer microfluidic channels and/or the one or more second layer microfluidic channels are straight lines.

Embodiment 17

The apparatus of any of embodiments 1-15, wherein each of the one or more first layer microfluidic channels and/or the one or more second layer microfluidic channels are curved lines.

Embodiment 18

The apparatus of any of embodiments 1-15, wherein each of the one or more first layer microfluidic channels and/or the one or more second layer microfluidic channels are wave-form lines.

Embodiment 19

The apparatus of any of embodiments 1-18, wherein the number of one or more first layer microfluidic channels is equal to the number of one or more second layer microfluidic channels.

Embodiment 20

The apparatus of any of embodiments 1-19, wherein the number of one or more first layer microfluidic channels and the number of one or more second layer microfluidic channels is 32.

Embodiment 21

The apparatus of any of embodiments 1-16, wherein each of the one or more first layer microfluidic channels and each of the one or more second layer microfluidic channels are straight lines.

Embodiment 22

The apparatus of embodiment 21, wherein the one or more first layer microfluidic channels overlap with the one or more second layer microfluidic channels to form a grid design comprising a plurality of squares, rectangles, parallelograms, or *rhombi*.

Embodiment 23

The apparatus of any of embodiments 1-22, wherein the cell analysis layer is about 10-15 µM, about 16-20 µM, or about 21-25 µM high.

Embodiment 24

The apparatus of any of embodiments 1-23, wherein the cell trap is about 10-12 µM, about 13-16 µM, or about 17-20 µM micrometer high.

Embodiment 25

The apparatus of any of embodiments 1-24, wherein the top hanging blocking structure is about 5-10 µM, about 11-15 µM, or about 16-20 µM high.

Embodiment 26

The apparatus of any of embodiments 1-25, wherein the cell analysis layer is about 15 µM high, the cell trap is about 12 µM high, and the top hanging blocking structure is about 8 µM high.

Embodiment 27

The apparatus of any of embodiments 1-26, wherein the first microfluidic control layer is about 10-15 µM, about 16-20 µM, or about 21-25 µM high.

Embodiment 28

The apparatus of any of embodiments 1-27, wherein the second microfluidic control layer is about 10-15 µM, about 16-20 µM, or about 21-25 µM high.

Embodiment 29

The apparatus of embodiment 3, the top hanging blocking structure closes the juxtaposed cell trap when the second layer microfluidic channel located directly above the top hanging blocking structure and/or the first layer microfluidic channel overlapping the second layer microfluidic channel located directly above the top hanging blocking structure is pressurized to at least about 15-20, about 21-25, about 26-30, about 31-35, about 36-40, about 41-45, about 46-50, or about 51-55 psi.

Embodiment 30

The apparatus of embodiment 3, wherein the top hanging blocking structure opens the juxtaposed cell trap when the second layer microfluidic channel located directly above the top hanging blocking structure and the first layer microfluidic channel overlapping the second layer microfluidic channel located directly above the top hanging blocking structure are pressurized to less than about 1-5, about 6-10, or about 11-15 psi.

Embodiment 31

The apparatus of embodiment 3, wherein the second layer microfluidic channels do not have the top hanging ridge structures, and the top hanging blocking structure closes the juxtaposed cell trap when the second layer microfluidic channel located directly above the top hanging blocking structure is pressurized to at least about 15-20, about 21-25, or about 26-30 psi and/or the first layer microfluidic channel overlapping the second layer microfluidic channel located directly above the top hanging blocking structure is pressurized to at least about 40-45, about 46-50, or about 51-55 psi.

Embodiment 32

The apparatus of embodiment 3, wherein the second layer microfluidic channels do not have the top hanging ridge structures, and the top hanging blocking structure closes the juxtaposed cell trap when the second layer microfluidic channel located directly above the top hanging blocking structure is pressurized to at least about 18 psi and/or the first layer microfluidic channel overlapping the second layer microfluidic channel located directly above the top hanging blocking structure is pressurized to at least about 50 psi.

Embodiment 33

The apparatus of embodiment 3, wherein the second layer microfluidic channels have the top hanging ridge structures, and the top hanging blocking structure closes the juxtaposed cell trap when the second layer microfluidic channel located directly above the top hanging blocking structure is pressurized to at least about 15-20, about 21-25, or about 26-30 psi and/or the first layer microfluidic channel overlapping the second layer microfluidic channel located directly above the top hanging blocking structure is pressurized to at least about 25-30 or about 31-35 psi.

Embodiment 34

The apparatus of embodiment 3, wherein the second layer microfluidic channels have the top hanging ridge, and the top hanging blocking structure closes the juxtaposed cell trap when the second layer microfluidic channel located directly above the top hanging blocking structure is pressurized to at least about 18 psi and/or the first layer microfluidic channel overlapping the second layer microfluidic channel located directly above the top hanging blocking structure is pressurized to at least about 30 psi.

Embodiment 35

The apparatus of embodiment 4, wherein the top hanging blocking structure closes the juxtaposed cell trap when both the second layer microfluidic channel located directly above the top hanging blocking structure and the first layer microfluidic channel overlapping the second layer microfluidic channel located directly above the top hanging blocking structure are pressurized to at least about 15-20, about 21-25, about 26-30, about 31-35, about 36-40, about 41-45, about 46-50, or about 51-55 psi.

Embodiment 36

The apparatus of embodiment 4, wherein the top hanging blocking structure opens the juxtaposed cell trap when the second layer microfluidic channel located directly above the top hanging blocking structure and/or the first layer microfluidic channel overlapping the second layer microfluidic channel located directly above the top hanging blocking structure is pressurized to less than about 1-5, about 6-10, or about 11-15 psi.

Embodiment 37

The apparatus of embodiment 4, wherein the second layer microfluidic channels do not have the top hanging ridge structures, and the top hanging blocking structure closes the juxtaposed cell trap when the second layer microfluidic channel located directly above the top hanging blocking structure is pressurized to at least about 15-20, about 21-25, or about 26-30 psi and the first layer microfluidic channel overlapping the second layer microfluidic channel located directly above the top hanging blocking structure is pressurized to at least about 40-45, about 46-50, or about 51-55 psi.

Embodiment 38

The apparatus of embodiment 4, wherein the second layer microfluidic channels do not have the top hanging ridge structures, and the top hanging blocking structure closes the juxtaposed cell trap when the second layer microfluidic channel located directly above the top hanging blocking structure is pressurized to at least about 18 psi and the first layer microfluidic channel overlapping the second layer microfluidic channel located directly above the top hanging blocking structure is pressurized to at least about 50 psi.

Embodiment 39

The apparatus of embodiment 4, wherein the second layer microfluidic channels have the top hanging ridge structures, and the top hanging blocking structure closes the juxtaposed cell trap when the second layer microfluidic channel located directly above the top hanging blocking structure is pressurized to at least about 15-20, about 21-25, or about 26-30 psi and the first layer microfluidic channel overlapping the second layer microfluidic channel located directly above the top hanging blocking structure is pressurized to at least about 25-30 or about 31-35 psi.

Embodiment 40

The apparatus of embodiment 4, wherein the second layer microfluidic channels have the top hanging ridge structures, and the top hanging blocking structure closes the juxtaposed cell trap when the second layer microfluidic channel located directly above the top hanging blocking structure is pressurized to at least about 18 psi and the first layer microfluidic channel overlapping the second layer microfluidic channel located directly above the top hanging blocking structure is pressurized to at least about 30 psi.

Embodiment 41

A method for screening and selecting a target cell within a population of cells, the method comprising:
 a) providing the population of cells,
 b) optionally, mutagenizing the population of cells,
 c) loading the mutagenized population of cells into the apparatus of any of the embodiments 1-40,
 d) conducting a bioassay to identify the target cell in the population of cells,
 e) isolating the target cell.

Embodiment 42

The method of embodiments 1-41, wherein isolating the target cell comprises:
 a) pressurizing all of the first layer microfluidic channels and all of the second layer microfluidic channels thereby closing all cell traps,
 b) opening only the cell trap containing the target cell by:
  A) sufficiently depressurizing only that second layer microfluidic channel which is directly above the cell trap containing the target cell,
  B) sufficiently depressurizing only that first layer microfluidic channel which is overlapping the microfluidic channel directly above the cell trap containing the target cell,
 c) extracting the target cell from the cell trap and collecting the target cell to off-chip reservoirs.

Embodiment 43

The method of embodiments 1-41, wherein isolating the target cell comprises:
 a) pressurizing all of the first layer microfluidic channels and all of the second layer microfluidic channels thereby closing all cell traps,
 b) opening all the cell traps except the cell trap containing the target cell by:
  A) sufficiently depressurizing all the second layer microfluidic channels except the second layer microfluidic channel which is directly above the cell trap containing the target cell, and
  B) sufficiently depressurizing all the first layer microfluidic channels except the first layer microfluidic channel which is overlapping the microfluidic channel directly above the cell trap containing the target cell,
  C) washing off the cells present in the all the cell traps except the cell trap containing the target cell,
 c) extracting the target cell from the cell trap of interest by:
  A) sufficiently depressurizing the second layer microfluidic channel which is directly above the cell trap containing the target cell, and/or
  B) sufficiently depressurizing the first layer microfluidic channel which is overlapping the microfluidic channel directly above the cell trap containing the target cell,
 d) extracting the target cell from the cell trap and collecting the target cell to off-chip reservoirs.

Embodiment 44

The method of embodiments 1-41, wherein the bioassay detects the presence of a protein, a lipid, or a metabolite in the target cell.

Embodiment 45

The method of embodiments 1-41, wherein the bioassay is designed to detect the ability of the target cell to grow in the presence or absence of an agent.

Embodiment 46

The method of embodiment 45, wherein the agent is an antibiotic, a growth inhibitor, or a metabolite.

Embodiment 47

The method of embodiment 44, wherein the protein is an enzyme, an antibody or a fragment thereof, or a pharmaceutically active protein.

Embodiment 48

The method of embodiments 1-41, wherein the population of cell comprises prokaryotic cells or eukaryotic cells.

Embodiment 49

The method of embodiment 48, wherein the prokaryotic cells comprise bacterial cells or cyanobacterial cells.

Embodiment 50

The method of embodiment 48, wherein the eukaryotic cells comprise yeast cells, fungal cells, protozoan cells, eukaryotic algal cells, or mammalian cells.

Embodiment 51

The method of embodiment 48, wherein the eukaryotic algal cells comprise *Tetraselmis suecica*.

Embodiment 52

The method of embodiment 48, wherein the eukaryotic cells comprise cultured mammalian cells or mammalian cells obtained from a mammal.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1—High Throughput Microfluidic Screening Apparatus Comprising 32 Microchannels in Each Microfluidic Control Layer In an embodiment of the invention, the high-throughput screening apparatus is made of PDMS. The apparatus consists of two functional layers; a microfluidic cell analysis layer and a control layer comprising of a first and a second microfluidic control layers (FIG. 1). The cell analysis layer (15 µM high) has 1024 cell traps (32×32 array), where either single or multiple cells can be captured, cultured, and analyzed.

In the mutant screening application, the number of cell traps determines the number of mutagenized cells that can be screened. Each cell trap consists of top-hanging structures having two different heights (FIG. 2). A backside semicircular structure (12 µM high, cell trap) is utilized to capture cells while a top hanging blocking structure (8 µM high) functions as a gate to the cell traps.

The gates for all cell traps typically remain open during cell loading, culturing, and analysis. During the selective cell extraction process, the top hanging blocking structure can be selectively opened to extract cells of particular interest from a specific cell trap while closing all other cell traps, for example, in the AND gate mode apparatus, or the top hanging blocking structure can be selectively opened to extract cells of from all but a specific cell trap of interest while closing the cell trap of interest, for example, in the OR gate mode apparatus.

The control layer is composed of the first and the second microfluidic control layers, each having 32 columns or rows of pneumatic or hydraulic control microfluidic channels. This control layer is utilized to individually address and control each of the 1024 cell traps, specifically the top hanging blocking structure as described above in the analysis layer for selective cell extraction.

In an AND gate mode apparatus, to extract cells from a particular cell trap, first, pressure is applied to both the row and column pneumatic control channels to close all cell traps in the apparatus. Then, only the row and the column covering the desired cell trap are released by removing the applied pressure from the channels, thus lifting the top hanging blocking structure that results in the cell trap to be opened. Among cell traps under these pressure-released regions, only the desired cell trap is open since all cell traps can be successfully blocked with only a column or a row control channel sufficiently pressurized (FIG. 4).

Thus, this scheme works as a microfluidic AND logic gate, where cell traps with no pressure to the column nor the row channel results in open cell trap (1 AND 1=1 (open)) but sites with at least one of the column and row channels pressurized results in closed cell trap (0 AND 1=0; 1 AND 0=0; 0 AND 0=0 (closed)). Cells inside this particular cell trap can be extracted and collected to off-chip reservoirs with backflow for further analysis.

Using this scheme, the number of microfluidic control channels can be minimized. For example, to control 1024 cell trap sites (32 by 32) individually, a conventional method would require 1024 individually controllable microfluidic control channels. However in this scheme, all 1024 cell traps can be controlled by 32+32 microfluidic control channels. The number of control channels can be further reduced by utilizing a microfluidic multiplexer.

Example 2—*Tetraselmis suecica* Screening

Figure 6:
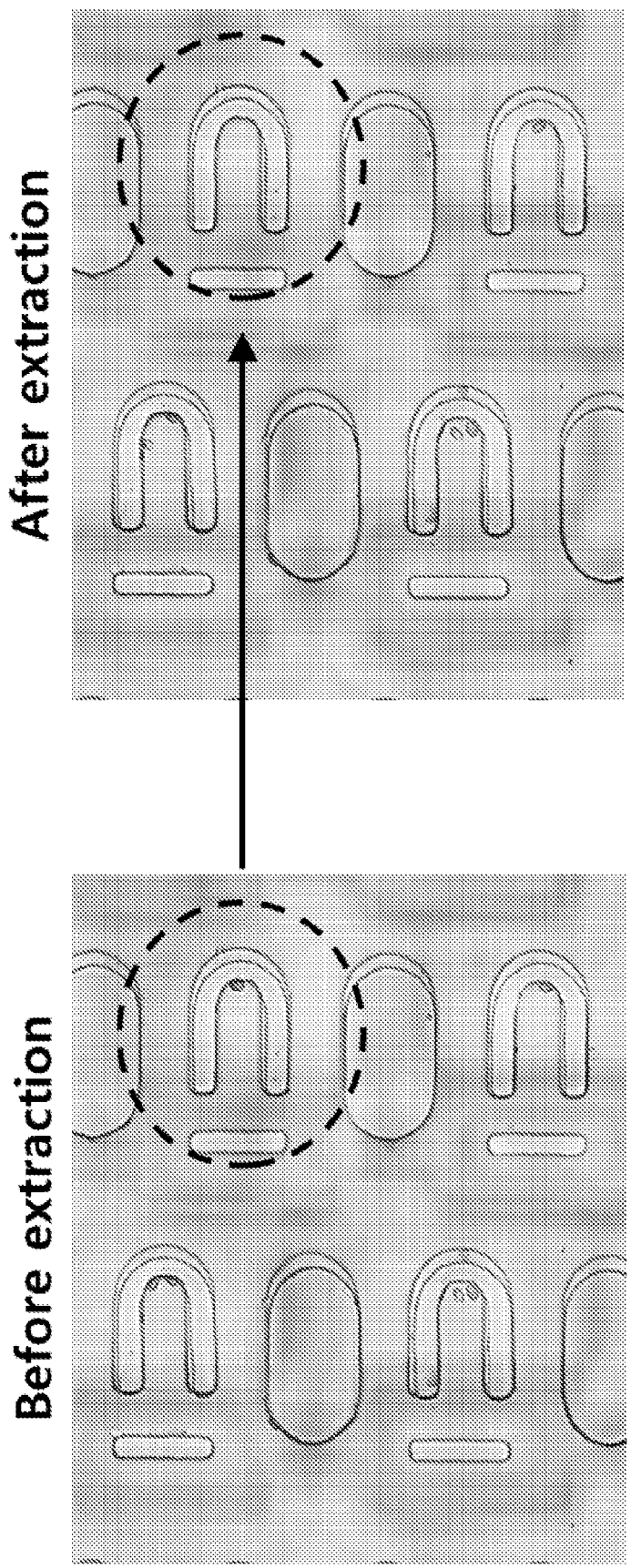
FIG. 6. Microscopic images showing selective extraction of cells from the apparatus. *Tetraselmis suecica* cell was successfully extracted from a particular cell trap (dashed circle) without affecting cells captured at other cell traps.

First, *Tetraselmis suecica* cells were loaded into the apparatus with the flow rate of 4~6 µl/min, followed by a flushing step to remove the uncaptured cells. As shown in FIG. 6, a single cell or multiple cells were successfully captured in each cell trap in the analysis layer.

During the culture and analysis period, the top hanging blocking structures stayed open to provide nutrients with culture media flowing freely through the cell traps.

In a AND gate mode apparatus, to extract the cells from a particular cell trap after analysis, all cell traps were blocked by actuating all control channels with pressure (30 psi), and only a particular cell trap (dashed circle) was opened by selectively releasing pressure from control channels covering that site. Using backflow (10~15 μl/min), *Tetraselmis suecica* cells inside this particular cell trap were successfully extracted without affecting cells captured at other cell traps.

Figure 7:
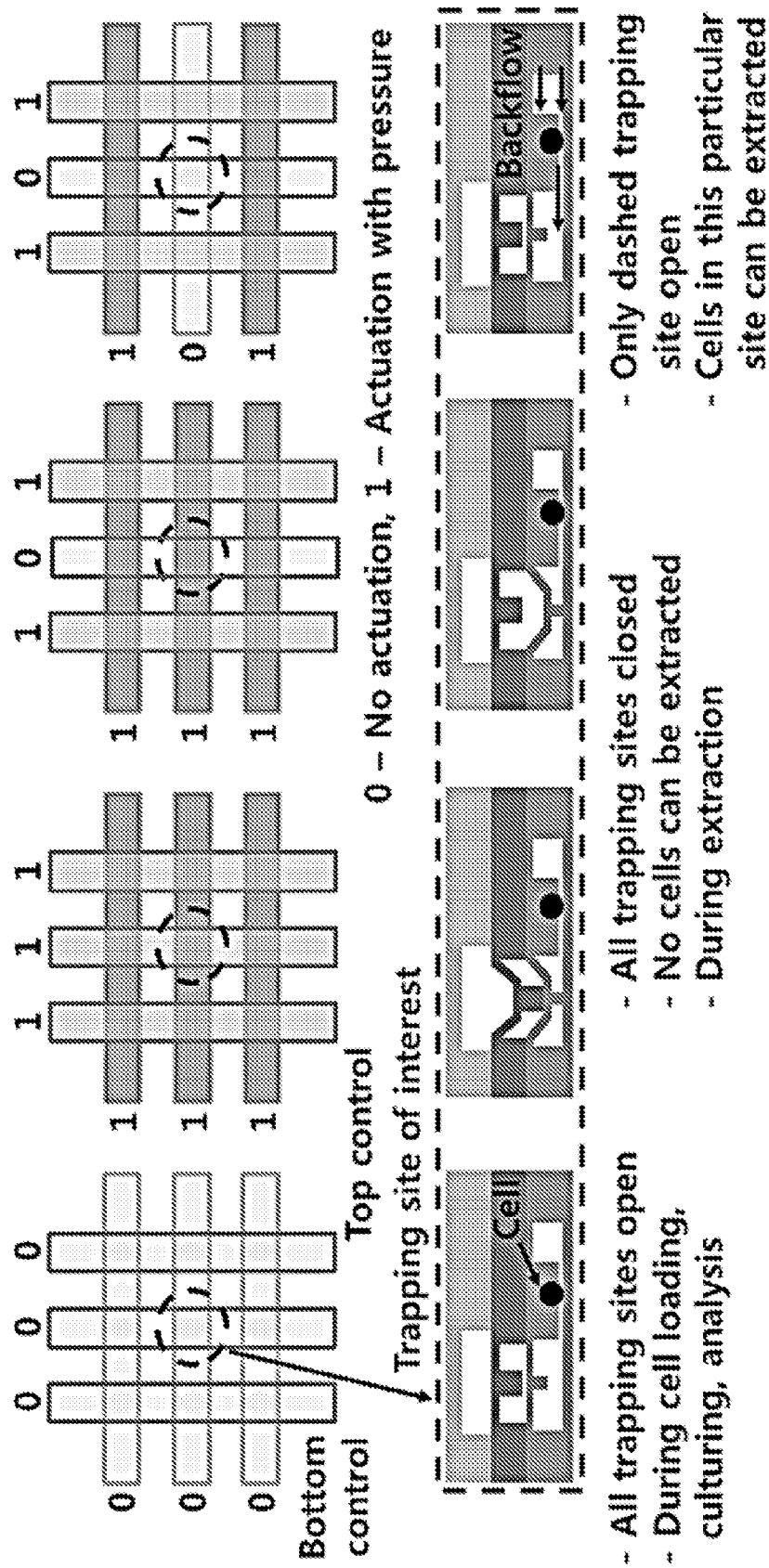
FIG. 7. Selective extraction of cells of interest in accordance with an embodiment of the current invention.

FIG. 7 shows the selective extraction of cells of interest in accordance with an embodiment of the invention.

The microfluidic AND logic scheme can be broadly utilized in other applications as well, where individual access to large arrays of pneumatically or hydraulically controllable microstructures are needed.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. N. E. Labrou, Random Mutagenesis Methods for In Vitro Directed Enzyme Evolution, Current Protein and Peptide Science, 11, 91 (2010).
2. L. L. Beer, E. S. Boyd, J. W. Peters, and M. C. Posewitz, Engineering Algae for Biohydrogen and Biofuel Production, Current Opinion in Biotechnology, 20, 264 (2009).
3. J. Fabregas, J. Abalde, C. Herrero, B. Cabezas, and M. Veiga, Growth of The Marine Microalga *Tetraselmis suecica* in Batch Cultures with Different Salinities and Nutrient Concentrations, Aquaculture, 42, 207 (1984).
4. U. Singh, R. Quintanilla, S. Grecian, K. Gee, M. Rao, and U. Lakshmipathy, Novel Live Alkaline Phosphatase Substrate for Identification of Pluripotent Stem Cells, Stem Cell Rev.; 8(3): 1021-1029 (2012).

We claim:

1. An apparatus for screening and selecting a target cell within a population of cells, the apparatus comprising:
    a first layer comprising a first top-hanging structure that is stationary and functions as a cell trap to trap a single cell or sub-population of cells, and a second top-hanging structure having a different height relative to the first top-hanging structure, wherein the second top-hanging structure is mobile and functions as a gate to open or close the cell trap;
    a second layer comprising a plurality of microfluidic channels in rows; and
    a third layer comprising the same number of microfluidic channels in rows as the second layer,
    wherein the microfluidic channel rows in the third layer are located in a perpendicular direction to the microfluidic channel rows in the second layer;
    wherein the second and third layers combine to function as a microfluidic logic AND gate where the microfluidic channels in the second layer and the third layer function as two inputs to the AND gate and the up and down movement of the second top-hanging gate structure is the output of the AND gate.

2. An apparatus for screening and selecting a target cell within a population of cells, the apparatus comprising:
    a) a first microfluidic control layer comprising one or more first layer microfluidic channels;
    b) a second microfluidic control layer comprising a one or more second layer microfluidic channels,
        wherein the one or more first layer microfluidic channels are not parallel to the one or more second layer microfluidic channels and each of the one or more first layer microfluidic channels overlaps with each of the one or more second layer microfluidic channels only once,
        and the one or more second layer microfluidic channels optionally contain top hanging ridge structures at every location where the one or more first layer microfluidic channels overlap with the one or more second layer microfluidic channels; and
    c) a microfluidic cell analysis layer comprising:
        i) a top hanging blocking structure located directly below every location where the first layer microfluidic channels overlap with the second layer microfluidic channels, and
        ii) a cell trap juxtaposed to each of the top hanging blocking structures.

3. The apparatus of claim 2, wherein the top hanging blocking structure closes the juxtaposed cell trap when the second layer microfluidic channel located directly above the top hanging blocking structure is sufficiently pressurized and/or the first layer microfluidic channel overlapping the second layer microfluidic channel located directly above the top hanging blocking structure is sufficiently pressurized, and
    wherein the top hanging blocking structure opens the cell trap when the second layer microfluidic channel located directly above the top hanging blocking structure and the first layer microfluidic channel overlapping the second layer microfluidic channel located directly above the top hanging blocking structure are sufficiently depressurized.

4. The apparatus of claim 2, wherein the top hanging blocking structure closes the juxtaposed cell trap when the second layer microfluidic channel located directly above the top hanging blocking structure is sufficiently pressurized and the first layer microfluidic channel overlapping the second layer microfluidic channel located directly above the top hanging blocking structure is sufficiently pressurized, and
    wherein the top hanging blocking structure opens the juxtaposed cell trap when the second layer microfluidic channel located directly above the top hanging blocking structure and/or the first layer microfluidic channel overlapping the second layer microfluidic channel located directly above the top hanging blocking structure is sufficiently depressurized.

5. The apparatus of claim 2 made wholly from an elastic material.

6. The apparatus of claim 2 made partly from an elastic material and partly from a rigid material.

7. The apparatus of claim 5, wherein the elastic material is an elastomer.

8. A method for screening and selecting a target cell within a population of cells, the method comprising:
    a) providing the population of cells, and
    b) optionally, mutagenizing the population of cells,
    c) loading the optionally mutagenized population of cells into the apparatus of claim 2,
    d) conducting a bioassay to identify the target cell in the population of cells, and
    e) isolating the target cell.

9. The method of claim 8, wherein isolating the target cell comprises:

a) pressurizing all of the first layer microfluidic channels and all of the second layer microfluidic channels thereby closing all cell traps,
b) opening only the cell trap containing the target cell by:
   i) sufficiently depressurizing only that second layer microfluidic channel which is directly above the cell trap containing the target cell,
   ii) sufficiently depressurizing only that first layer microfluidic channel which is overlapping the microfluidic channel directly above the cell trap containing the target cell, and
c) extracting the target cell from the cell trap and collecting the target cell to off-chip reservoirs.

10. The method of claim 8, wherein isolating the target cell comprises:
a) pressurizing all of the first layer microfluidic channels and all of the second layer microfluidic channels thereby closing all cell traps,
b) opening all the cell traps except the cell trap containing the target cell by:
   i) sufficiently depressurizing all the second layer microfluidic channels except the second layer microfluidic channel which is directly above the cell trap containing the target cell, and
   ii) sufficiently depressurizing all the first layer microfluidic channels except the first layer microfluidic channel which is overlapping the microfluidic channel directly above the cell trap containing the target cell, and
   iii) washing off the cells present in all the cell traps except the cell trap containing the target cell,
c) extracting the target cell from the cell trap of interest by:
   i) sufficiently depressurizing the second layer microfluidic channel which is directly above the cell trap containing the target cell, and/or
   ii) sufficiently depressurizing the first layer microfluidic channel which is overlapping the microfluidic channel directly above the cell trap containing the target cell, and
d) extracting the target cell from the cell trap and collecting the target cell to off-chip reservoirs.

11. The method of claim 8, wherein the bioassay detects the presence of a protein, a lipid, or a metabolite in the target cell.

12. The method of claim 8, wherein the bioassay is designed to detect the ability of the target cell to grow in the presence or absence of an agent.

13. The method of claim 12, wherein the agent is an antibiotic, a growth inhibitor, or a metabolite.

14. The method of claim 11, wherein the protein is an enzyme, an antibody or a fragment thereof, or a pharmaceutically active protein.

15. The method of claim 8, wherein the population of cells comprises prokaryotic cells or eukaryotic cells.

16. The method of claim 15, wherein the prokaryotic cells comprise bacterial cells or cyanobacterial cells.

17. The method of claim 15, wherein the eukaryotic cells comprise yeast cells, fungal cells, protozoan cells, eukaryotic algal cells, or mammalian cells.

18. The method of claim 15, wherein the eukaryotic algal cells comprise *Tetraslimis suecica*.

19. The method of claim 15, wherein the eukaryotic cells comprise cultured mammalian cells or mammalian cells obtained from a mammal.

* * * * *